US009521997B2

(12) United States Patent
Hawkins et al.

(10) Patent No.: US 9,521,997 B2
(45) Date of Patent: *Dec. 20, 2016

(54) METHODS AND DEVICES FOR TISSUE RETRACTION

(71) Applicant: DePuy Synthes Products, Inc., Raynham, MA (US)

(72) Inventors: John Riley Hawkins, Cumberland, RI (US); Christopher Ramsay, West Wareham, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/333,565

(22) Filed: Jul. 17, 2014

(65) Prior Publication Data

US 2014/0330085 A1    Nov. 6, 2014

Related U.S. Application Data

(63) Continuation of application No. 13/435,355, filed on Mar. 30, 2012, now Pat. No. 8,821,394.

(51) Int. Cl.
*A61B 17/02* (2006.01)
*A61B 17/00* (2006.01)

(52) U.S. Cl.
CPC .... *A61B 17/0293* (2013.01); *A61B 2017/0092* (2013.01); *A61B 2017/00407* (2013.01)

(58) Field of Classification Search
CPC ... A61B 17/025; A61B 17/02; A61B 17/0293; A61B 17/3423; A61B 17/1671; A61B 17/1757; A61B 19/5202; A61B 2019/462; A61B 2017/00477; A61B 2017/0256; A61B 2017/0262; A61B 2017/2923; A61B 2017/0046; A61B 2017/3464

(Continued)

(56) References Cited

U.S. PATENT DOCUMENTS 2,083,573 A    6/1937  Morgan
5,125,396 A    6/1992  Ray
(Continued)

FOREIGN PATENT DOCUMENTS

CN    2381274 Y    6/2000
CN    1735380 A    2/2006
(Continued)

OTHER PUBLICATIONS

International Search Report and Written Opinion for PCT Application No. PCT/US13/33875 mailed Jul. 3, 2013 24 pages.

(Continued)

*Primary Examiner* — Pedro Philogene
(74) *Attorney, Agent, or Firm* — Nutter McClennen & Fish LLP

(57) ABSTRACT

Methods and devices are provided for retracting tissue. In one exemplary embodiment, a retractor is provided that includes a base, a plurality of blades extending from the base, and an actuator coupled to the base and operatively connected to the blades. The actuator can be configured to be actuated to move the blades relative to the base, thereby allowing the blades to retract tissue. The actuator can be self-locking so as to allow the blades to be freely movable within their entire range of motion relative to the base through actuation of the actuator without using another mechanism to lock the blades in a fixed position and to unlock the blades from the fixed position. The retractor can be formed from one or more radiolucent materials.

20 Claims, 13 Drawing Sheets

(58) Field of Classification Search
USPC ............... 606/214, 201, 208, 210, 215, 219, 205,606/245, 213, 231–235
See application file for complete search history.

(56) References Cited

U.S. PATENT DOCUMENTS

| | | | |
|---|---|---|---|
| 5,509,893 | A | 4/1996 | Pracas |
| 5,906,620 | A | 5/1999 | Nakao et al. |
| 6,074,343 | A | 6/2000 | Nathanson et al. |
| 7,195,592 | B2 * | 3/2007 | Ravikumar ............ A61B 17/02 600/219 |
| 7,524,285 | B2 * | 4/2009 | Branch .............. A61B 17/0206 600/214 |
| 7,556,600 | B2 * | 7/2009 | Landry .............. A61B 17/0293 600/231 |
| 7,594,888 | B2 | 9/2009 | Raymond et al. |
| 7,766,927 | B2 | 8/2010 | Dan |
| 7,780,594 | B2 | 8/2010 | Hutton |
| 7,931,589 | B2 | 4/2011 | Cohen et al. |
| 7,976,463 | B2 | 7/2011 | Dewey et al. |
| 7,981,031 | B2 * | 7/2011 | Frasier .................. A61B 17/02 600/224 |
| 8,038,611 | B2 | 10/2011 | Raymond et al. |
| 8,550,995 | B2 | 10/2013 | Frasier et al. |
| 8,821,394 | B2 * | 9/2014 | Hawkins ............ A61B 17/0293 600/214 |
| 2005/0159650 | A1 | 7/2005 | Raymond et al. |
| 2005/0165281 | A1 | 7/2005 | Ravikumar et al. |
| 2006/0052672 | A1 | 3/2006 | Landry et al. |
| 2006/0229648 | A1 | 10/2006 | Dan |
| 2007/0156026 | A1 | 7/2007 | Frasier et al. |
| 2008/0262318 | A1 | 10/2008 | Gorek et al. |
| 2010/0228096 | A1 | 9/2010 | Weisenburgh, II et al. |
| 2010/0286486 | A1 | 11/2010 | Parker et al. |
| 2011/0144687 | A1 | 6/2011 | Kleiner |
| 2011/0160585 | A1 | 6/2011 | Akyuz et al. |
| 2011/0184447 | A1 | 7/2011 | Leibowitz et al. |
| 2011/0313256 | A1 | 12/2011 | Raymond et al. |
| 2013/0261402 | A1 | 10/2013 | Hawkins et al. |

FOREIGN PATENT DOCUMENTS

| | | |
|---|---|---|
| CN | 1913834 A | 2/2007 |
| CN | 1972635 A | 5/2007 |
| WO | 96/28083 A1 | 9/1996 |
| WO | 2007/035187 A2 | 3/2007 |
| WO | 2008/131084 A2 | 10/2008 |
| WO | 2009/050240 A1 | 4/2009 |
| WO | 2011/059498 A1 | 5/2011 |
| WO | 2012/026981 A1 | 3/2012 |

OTHER PUBLICATIONS

Chinese Office Action for Application No. 201380018122.7, issued Jan. 29, 2016 (9 pages).
Supplementary European Search Report for Application No. 13768274.6, issued Mar. 1, 2016 (9 pages).

* cited by examiner

METHODS AND DEVICES FOR TISSUE RETRACTION

CROSS-REFERENCE TO RELATED APPLICATIONS

The present application is a continuation of U.S. patent application Ser. No. 13/435,355 filed on Mar. 30, 2012, which is hereby incorporated herein by reference in its entirety.

FIELD OF THE INVENTION

The present invention relates generally to methods and devices for tissue retraction, and in particular to bladed retractors and methods for use.

BACKGROUND OF THE INVENTION

In surgical procedures, it is preferable to minimize or reduce trauma to the patient and damage to tissue. To achieve this result, surgeons try to keep incisions as small as possible. However, it is usually necessary that the surgeon have a clear view of the operating field.

A variety of retractors are available to keep an incision open and provide a clear view of the operating field. Retractors are used in surgical operations to reposition muscular tissue, vessels, nerves, and other tissue with the aid of retractor blades, thereby providing access to the site of the operation. Surgical retractors are particularly important in performing surgical procedures that involve the spinal column, where access to the surgical site can be obtained, for example, through a posterior, posterior-lateral, anterior, lateral, or an anterior-lateral approach.

Retraction can be performed in a variety of ways. In some embodiments, a step-wise dilation of the surgical incision can be performed to gradually dilate the muscles and tissues to the required size to insert the retractor. Step-wise dilation can involve the use of a series of dilators or cannulae with successively larger diameters. This method involves first inserting the smallest dilator or cannula into an incision. Then a second dilator or cannula, with a slightly larger diameter, is slid over the smaller dilator or cannula and into the incision, thereby causing the incision to expand to the slightly larger diameter of the second dilator or cannula. This process can be repeated using a series of dilators or cannulae with successively larger diameters, until the incision is large enough to allow for insertion of the retractor. Once positioned, the retractors produce a small surgical site or window.

In some embodiments, a retractor can include multiple blades attached to a frame. The blades can be inserted into tissue and moved apart from one another to retract the tissue. However, moving the blades apart from one another can be cumbersome depending on where access to the surgical site is obtained, e.g., awkward positioning of the surgeon relative to the retractor during lateral approach to a spine. It can also be difficult to adjust the blades to a particular desired position without moving the blades apart from one another too much, thereby causing problem(s) such as harming nearby tissue or pushing against a nerve.

Accordingly, a need exists for improved methods and devices for tissue retraction.

SUMMARY OF THE INVENTION

In one embodiment, a surgical device is provided that includes a base, a plurality of retractor blades having a proximal end coupled to the base and a distal portion extending distally from the base, and an actuator coupled to the base. The blades are configured to move radially relative one another to move between a collapsed position and an expanded position in which the blades define a working channel for receiving an instrument therethrough and in which a diameter of the working channel is greater than the diameter of the working channel when the blades are in the collapsed position. The actuator is configured to rotate relative to the base to cause the blades to move between the collapsed and expanded positions. In an exemplary embodiment, the base, the blades, and the actuator can be formed from a radiolucent material.

The actuator can have a variety of configurations. For example, the actuator can be seated in the base and can be operatively connected to the proximal ends of the blades. In one embodiment, the actuator can be self-locking such that the actuator is configured to freely move the blades between the collapsed and expanded positions without requiring actuation of a release mechanism. The actuator can be configured such that rotating the actuator in a first direction moves the blades to the collapsed position, and rotating the actuator in a second direction opposite to the first direction moves the blades to the expanded position. In an exemplary embodiment, the actuator can include a scroll gear, e.g., a self-locking scroll gear. In another exemplary embodiment, the actuator can be in the form of a ring disposed within a track formed in the base.

The blades can also have a variety of configurations. In one embodiment, when the blades are in the collapsed position at least one of the blades can have an inner surface facing an outer surface of at least another one of the blades such that the at least one of the blades and the at least another one of the blades overlap.

In another embodiment, a surgical device is provided that includes a base and a plurality of retractor blades extending from the base. The plurality of retractor blades can have a collapsed position and an expanded position. The plurality of retractor blades in the collapsed position can overlap one another such that the plurality of retractor blades define a single working channel having a closed cylindrical shape. The plurality of retractor blades in the expanded position are spaced a distance apart from one another. In one embodiment, when the plurality of retractor blades are in the collapsed position, at least one of the plurality of retractor blades is positioned radially inward of at least another one of the plurality of retractor blades.

The surgical device can also include an actuator coupled to the base. In one embodiment, the actuator can be configured to rotate relative to the base to cause the plurality of retractor blades to move between the collapsed and expanded positions. In an exemplary embodiment, the actuator can include a self-locking scroll gear.

In another embodiment, a surgical device is provided that includes a base, a plurality of retractor blades extending from the base and configured to retract tissue, and a self-locking actuator coupled to the base. Each of the blades have a proximal end coupled to the base. The blades are configured to move radially toward and away from one another. The actuator, e.g., a scroll gear, is configured to move relative to the base to cause the blades to move radially toward and away from one another, and the actuator is configured to self-lock the blades in any selected position relative to one another within a range of movement of the blades.

The actuator can vary in any number of ways. For example, the actuator can be configured to self-lock the blades in any selected position relative to one another by moving the actuator relative to the base without actuation of a lock mechanism, and the blades can be configured to unlock by moving the actuator relative to the base without actuation of a release mechanism. In one embodiment, the actuator can be configured to rotate relative to the base to cause the blades to move toward and away from one another.

In another aspect, a surgical method is provided that includes inserting a retractor through an incision formed in tissue, and rotating an actuator of the retractor in a first direction relative to a base of the retractor to cause blades of the retractor that are coupled to the base to move radially away from one another to expand the incision and to form a working channel that provides access to a body cavity.

The method can have any number of variations. For example, the actuator can self-lock to lock the blades in a fixed position relative to one another. The actuator can be rotated relative to the base without actuating a release mechanism. For another example, the actuator can be rotated in a second direction opposite to the first direction to cause the blades to move radially toward one another. For still another example, one of the blades can be coupled to a fixed support of the retractor. The one of the blades can remain stationary when the actuator is rotated in the first direction. For yet another example, after expanding the incision, an area including the incision can be radioimaged to produce a radiographic image. The base, the blades, and the actuator can be radiolucent such that the base, the blades, and the actuator are invisible in the radiographic image.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
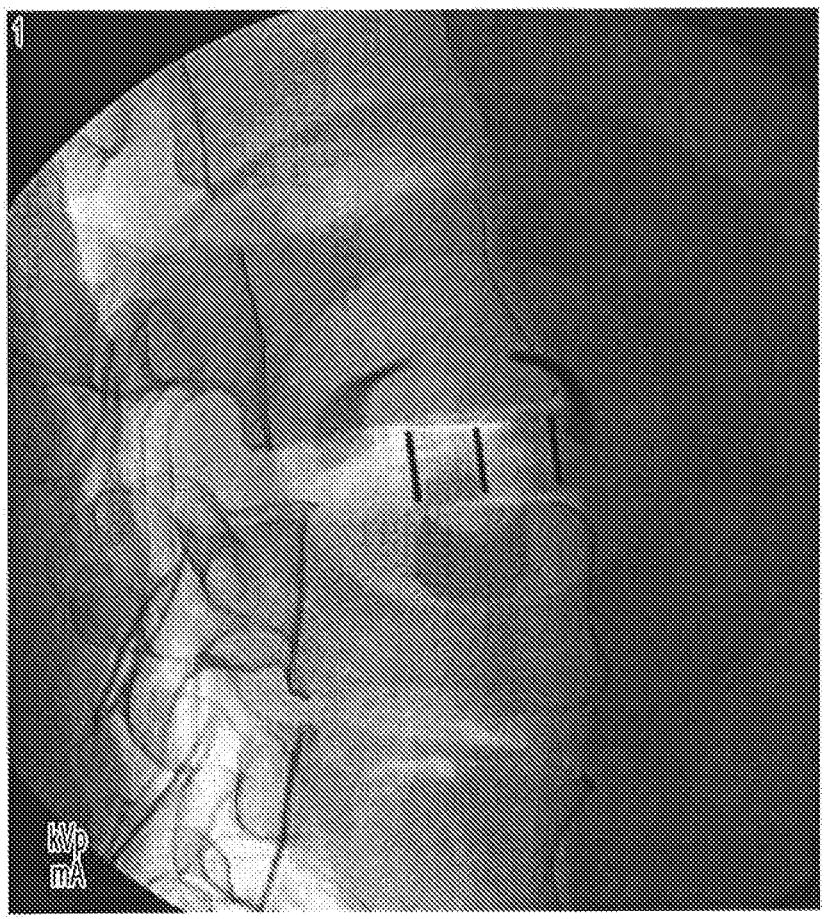
FIG. 1 is an x-ray image of one embodiment of a retractor formed from a radiolucent material retracting tissue adjacent to a spine.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for tissue retraction. In general, the methods and devices can allow tissue to be retracted without the need to lock the retractor in place and/or without the retractor leaving a radiographic footprint. In an exemplary embodiment, a retractor is provided that includes a base, a plurality of blades extending from the base, and an actuator coupled to the base and operatively connected to the blades. The actuator can be configured to be actuated to move the blades relative to the base, thereby allowing the blades to retract tissue. The actuator can be self-locking so as to allow the blades to be freely movable within their entire range of movement relative to the base through actuation of the actuator without using another mechanism to lock and unlock the blades relative to the base. In other words, when the actuator is being actuated, e.g., moved relative to the base, the actuator can cause the blades to move relative to the base, and when the actuator is not being actuated, e.g., the actuator is not moving relative to the base, the blades can be locked in a fixed position relative to the base without the need for a separate locking mechanism. A single actuator can therefore both move the blades relative to the base and lock the blades in a fixed position relative thereto, thereby simplifying use of the retractor. The actuator can allow for predictable control of blade position because once the actuator stops being actuated, the blades can be automatically locked in position without a risk of the blades shifting position after the blades and without a need for a locking mechanism.

The retractors disclosed herein can be formed from a variety of materials. Non-limiting examples of materials that can form a retractor include metals, polymers, and combinations thereof. Non-limiting examples of metals include titanium and stainless steel. Non-limiting examples of polymers include polyether ether ketone (PEEK), ultra-high-molecular-weight polyethylene (UHMPE), polyoxymethylene (POM) such as Delrin® available from DuPont of Wilmington, Del., Radel® polyphenylsulfone (Radel PPSU) available from Solvay S.A. of Ixelles, Brussels, Belgium, and carbon fiber reinforced polymers (CRFP) such as PEEK reinforced with carbon fibers. In an exemplary embodiment, the retractor can be formed from one or more radiolucent polymers, e.g., PEEK, which can allow the retractor to be substantially invisible in a radiographic image, e.g., an x-ray. A radiolucent retractor can facilitate inspection of a patient's anatomy and other objects in a radiographic image, e.g., without the retractor appearing dark on the image and hindering visualization of objects located behind the dark retractor and/or without reflections from blades of the retractor creating a bright spot within a working channel defined by the retractor blades and hindering visualization of objects located within or beyond a distal end of the working channel.

Figure 2:
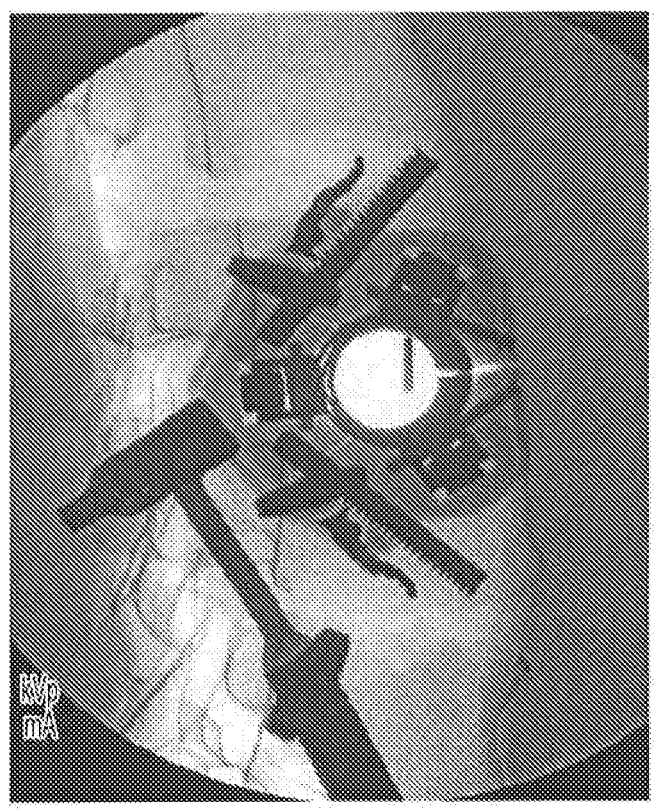
FIG. 2 is an x-ray image of one embodiment of a retractor formed from a non-radiolucent material retracting tissue adjacent to a spine.

Any portion of the retractor can be formed from a radiolucent material(s). At least a portion of the retractor within a zone of visualization can be formed from a radiolucent material(s), e.g., retractor blades formed from a radiolucent material(s) so as to make the retractor blades substantially invisible in a radiographic image and help prevent bright radioimage glare within a working channel defined by the blades. In an exemplary embodiment, the entire retractor can be formed from a radiolucent material(s) so as to make the entire retractor substantially invisible in a radiographic image. A retractor being entirely formed from a radiolucent material(s) also allows the retractor to be 100% disposable. While it is desirable to have retractors formed from a radiolucent material(s), the use of such materials with surgical retractors can be difficult due to the use of numerous parts and moving parts. The retractors disclosed herein are particularly advantageous as they utilize a relatively small number of moving parts, thus allowing all or least a substantial portion thereof to be formed while allowing integrity of the device to be maintained. FIG. 1 shows an example of an x-ray of a spine with a retractor that is formed entirely from a radiolucent material(s) and that is retracting tissue adjacent the spine. The retractor of FIG. 1 is substantially invisible in the x-ray. In contrast, FIG. 2 (prior art) shows an example of an x-ray of a spine with a retractor that is not formed from radiolucent material(s) retracting tissue adjacent the spine. The retractor of FIG. 2 is plainly visible as a dark object in the x-ray.

FIGS. 3-10 illustrate an exemplary embodiment of a retractor 10 configured to retractor tissue. As shown, the retractor 10 can include a base 12, an actuator 14, and a plurality of retractor blades 16a, 16b, 16c, 16d, 16e, 16f. Although the retractor 10 in this illustrated embodiment includes six blades 16a, 16b, 16c, 16d, 16e, 16f, the retractor can include any number of blades, e.g., two, three, four, five, seven, etc.

Figure 6:
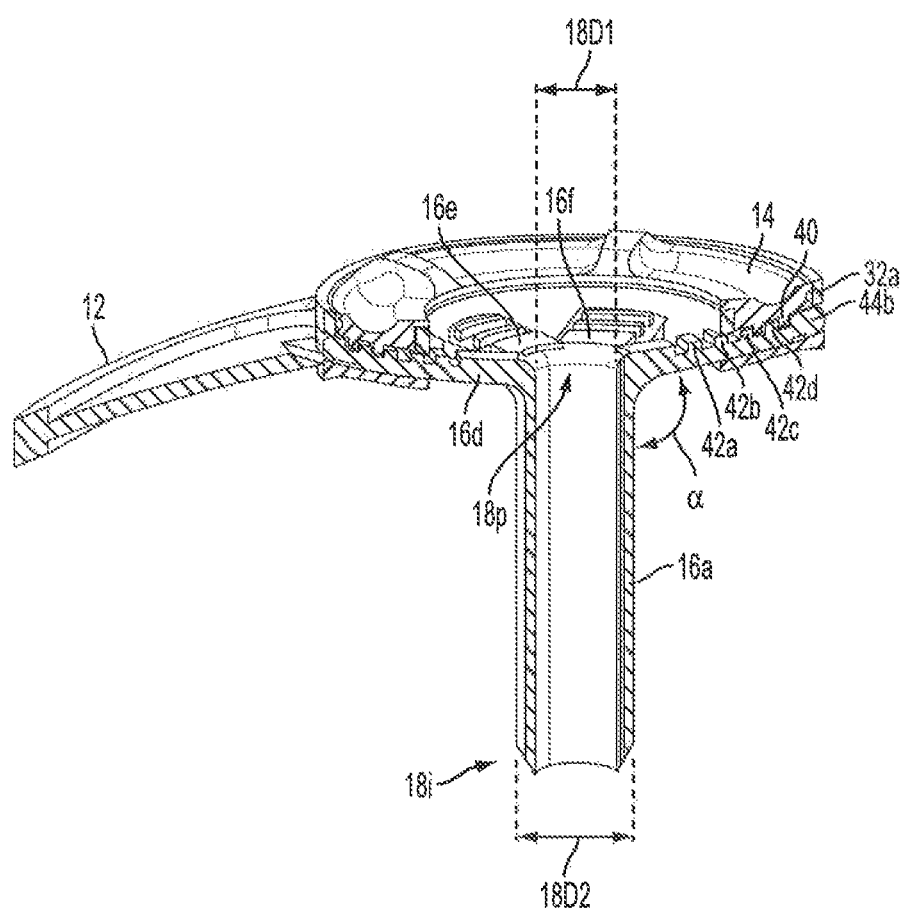
FIG. 6 is a cross-sectional view of the retractor of FIG. 5.
Figure 7:
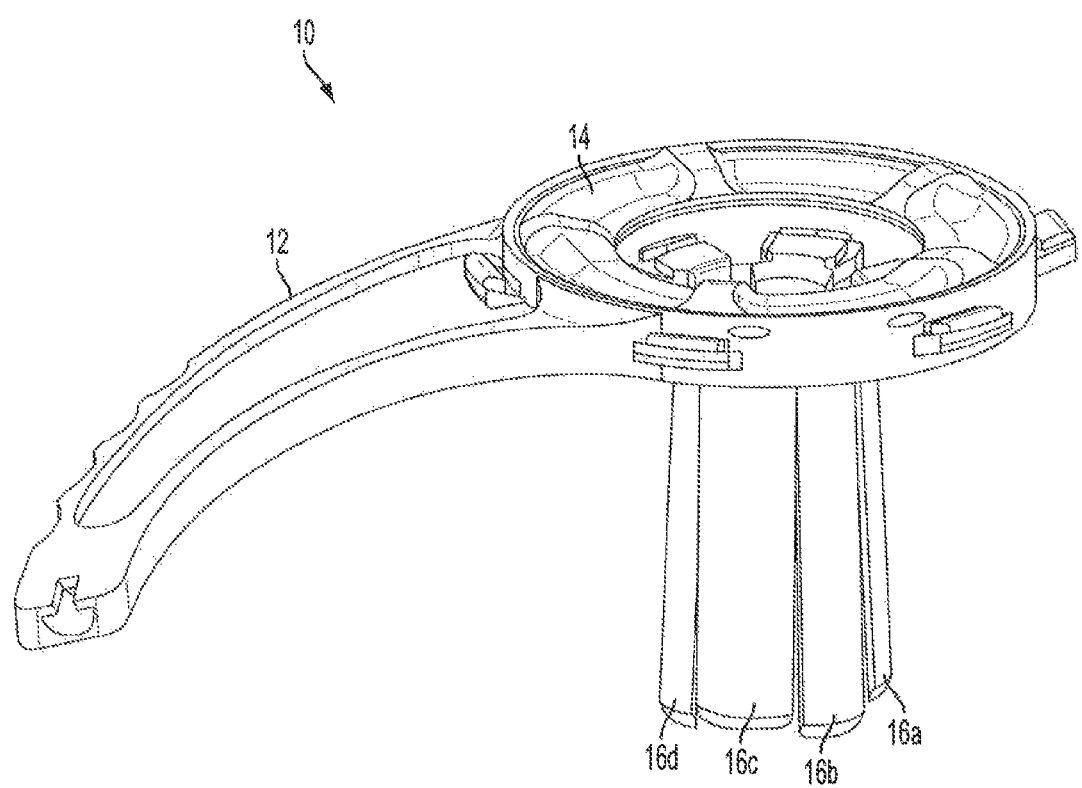
FIG. 7 is a perspective view of the retractor of FIG. 3 in an open position with blades of the retractor partially expanded.
Figure 8:
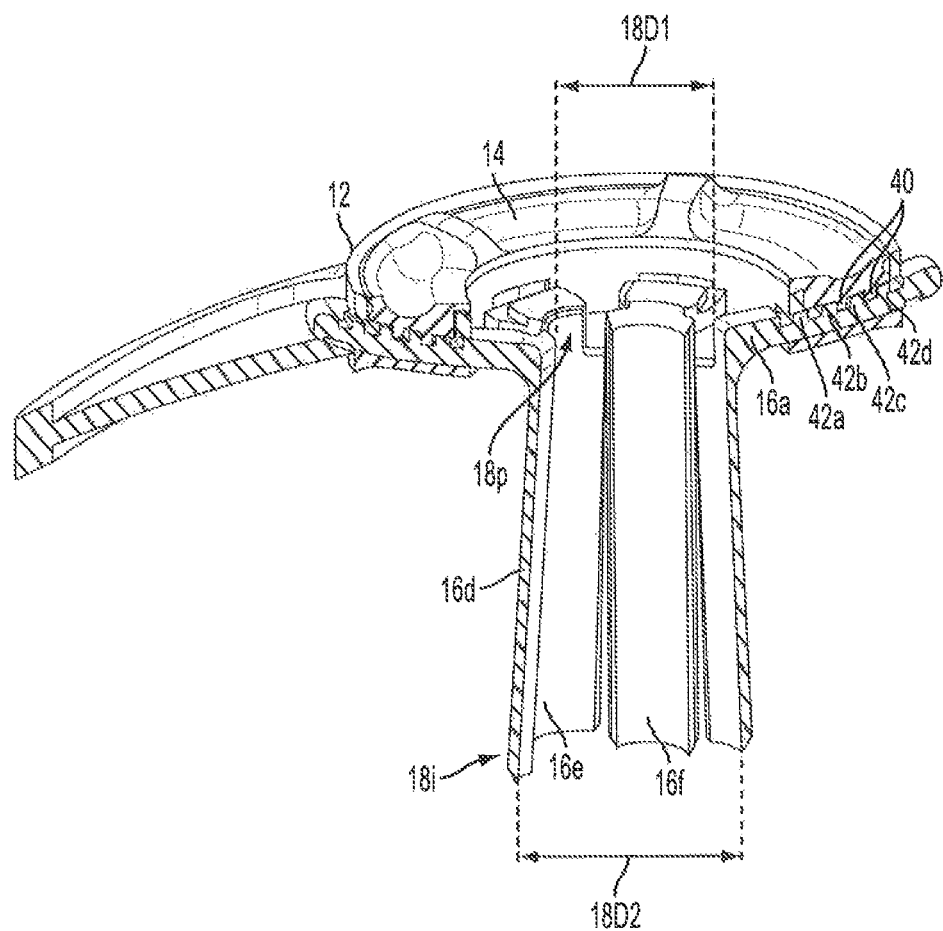
FIG. 8 is a cross-sectional view of the retractor of FIG. 7.
Figure 9:
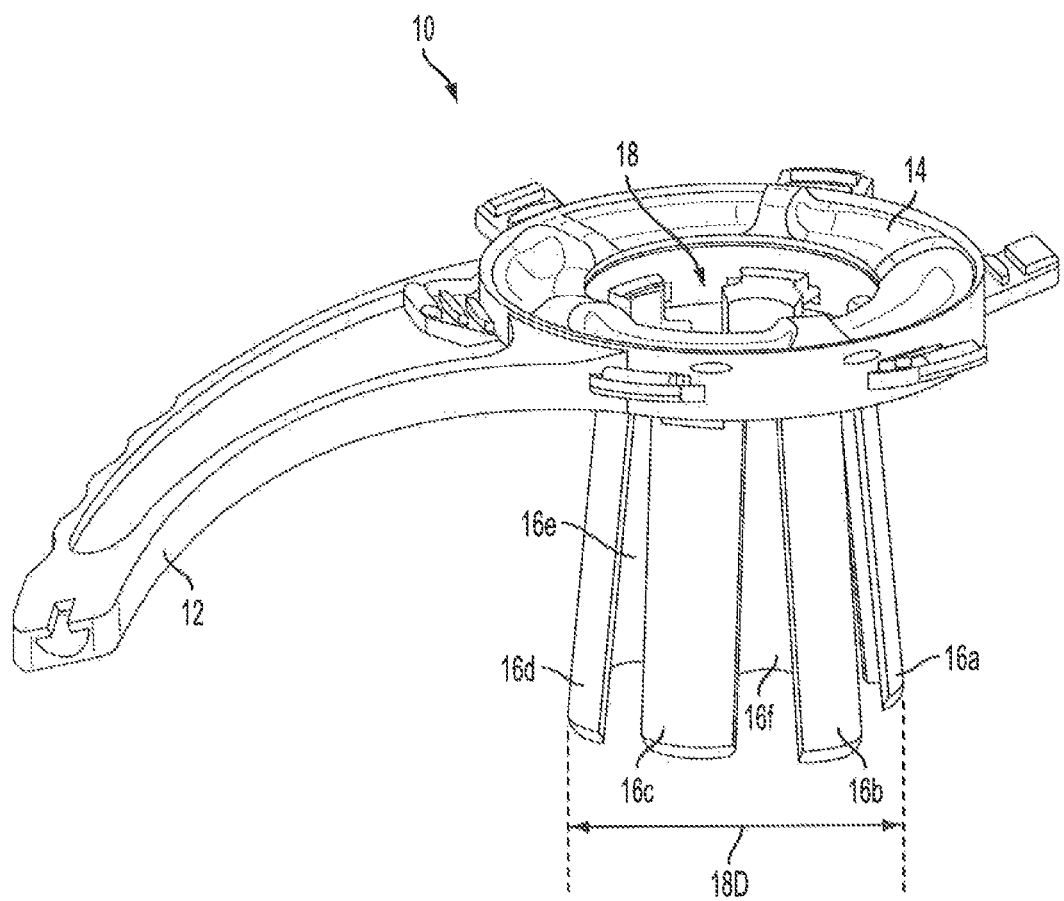
FIG. 9 is a perspective view of the retractor of FIG. 3 in an open position with blades of the retractor fully expanded.
Figure 10:
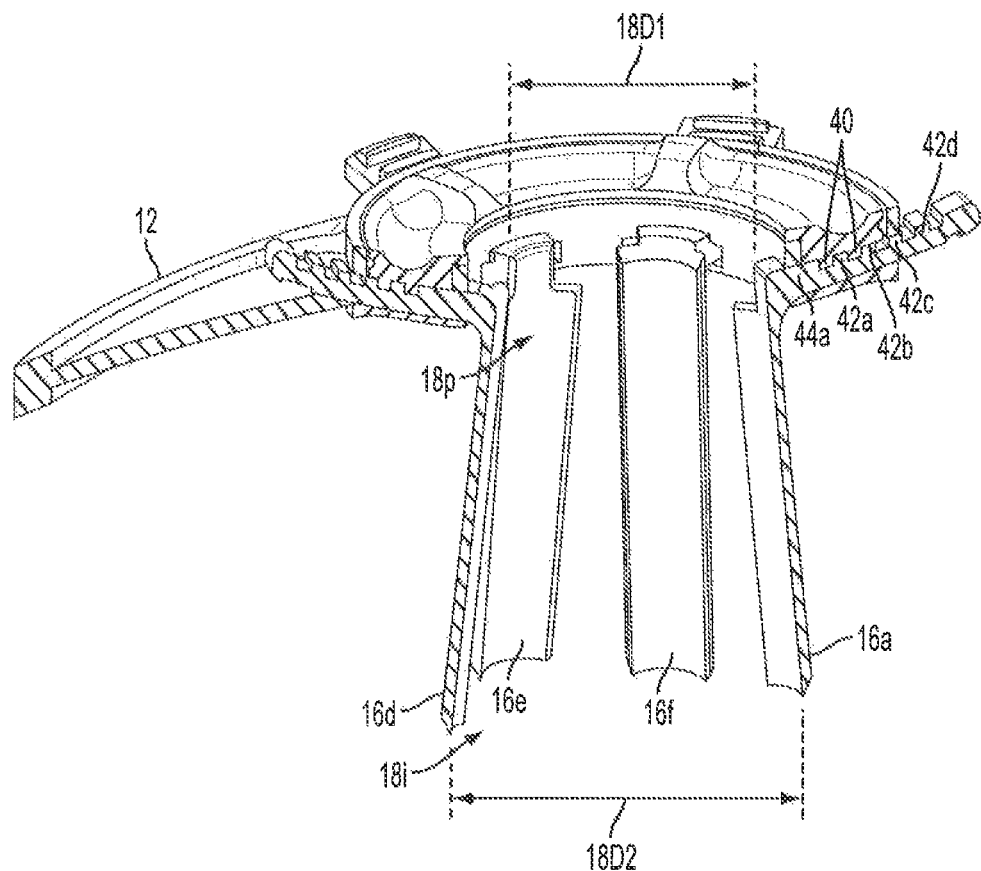
FIG. 10 is a cross-sectional view of the retractor of FIG. 9.

The retractor 10 can be configured to be movable between a closed position, shown in FIGS. 3-6, and an open position, shown in FIGS. 7-10. As discussed further below, the actuator 14 can be configured to move the retractor 10 between the open and closed positions. Generally, in the closed position, the blades 16a, 16b, 16c, 16d, 16e, 16f can be in a collapsed position in which they are at a first end of their full range of movement and are at a closest distance to one another. In this position, the blades 16a, 16b, 16c, 16d, 16e, 16f can define a working channel 18 having a diameter 18D at its smallest size. Generally, in the open position, the retractor 10 can be in an expanded position in which the working channel 18 has a greater diameter 18D than when the retractor 10 is in the closed position. When the retractor 10 is in the open or expanded position, the blades 16a, 16b, 16c, 16d, 16e, 16f can be fully open or partially open. In a fully open position, as shown in FIGS. 9 and 10, the blades 16a, 16b, 16c, 16d, 16e, 16f are at a second end of their full range of movement in which they are at farther distance apart from one another and thereby define the diameter 18D of the working channel 18 at its greatest size. In a partially open position, as shown in FIGS. 7 and 8, the blades 16a, 16b, 16c, 16d, 16e, 16f are at an intermediate position between the first and second ends of their full range of movement. Although FIGS. 7 and 8 illustrate the blades 16a, 16b, 16c, 16d, 16e, 16f in a particular intermediate position, the blades 16a, 16b, 16c, 16d, 16e, 16f can be positioned at any selected intermediate position between the closed and fully open positions. The distance between the blades 16a, 16b, 16c, 16d, 16e, 16f can therefore be increased or decreased to any desired extent, thereby allowing the retractor 10 to adjust to an almost infinite number of positions, which can allow the retractor 10 to be used with a variety of differently sized patients, with a variety of differently sized tissue, and with a variety of differently sized instruments inserted through the working channel 18.

Figure 11:
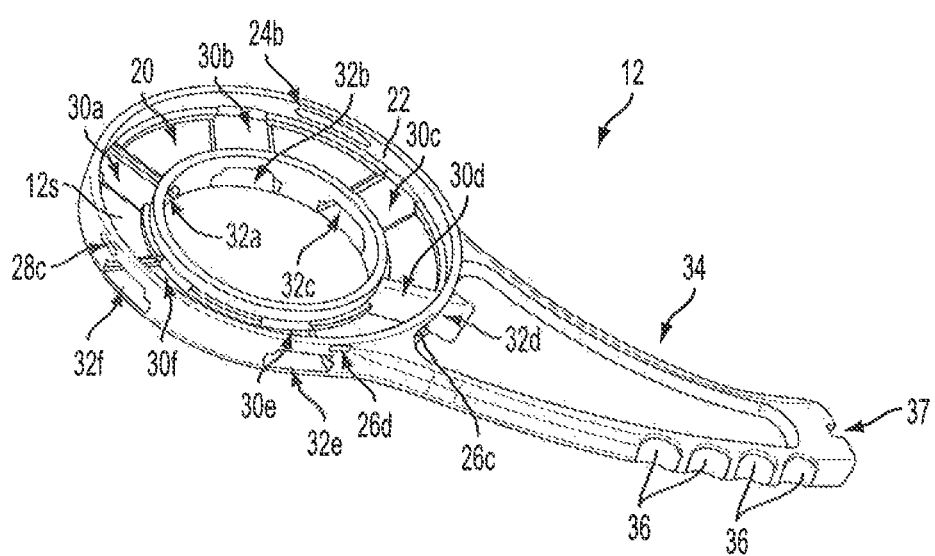
FIG. 11 is a perspective view of a base of the retractor of FIG. 3.

The base 12, which is illustrated as a standalone element in FIG. 11, can have a variety of sizes, shapes, and configurations. The base 12 can include a track 20 formed therein that can be configured to seat the actuator 14. The actuator 14 seated in the track 20 can be configured to move relative to the base 12, as discussed further below. As shown, the track 20 can be recessed within the base 12 to allow the actuator 14 to sit flush or sub-flush within the base 12, which can lower a profile of the retractor 10 for ease of packaging and ease of use. In the illustrated embodiment, as shown in FIGS. 3-10, a user-manipulatable portion of the actuator 14 can extend outside of the base 12 to facilitate movement thereof, as also discussed further below. Also, the track 20 can be circular, which can facilitate rotation of the actuator 14 within the track 20 relative to the base 12.

Figure 3:
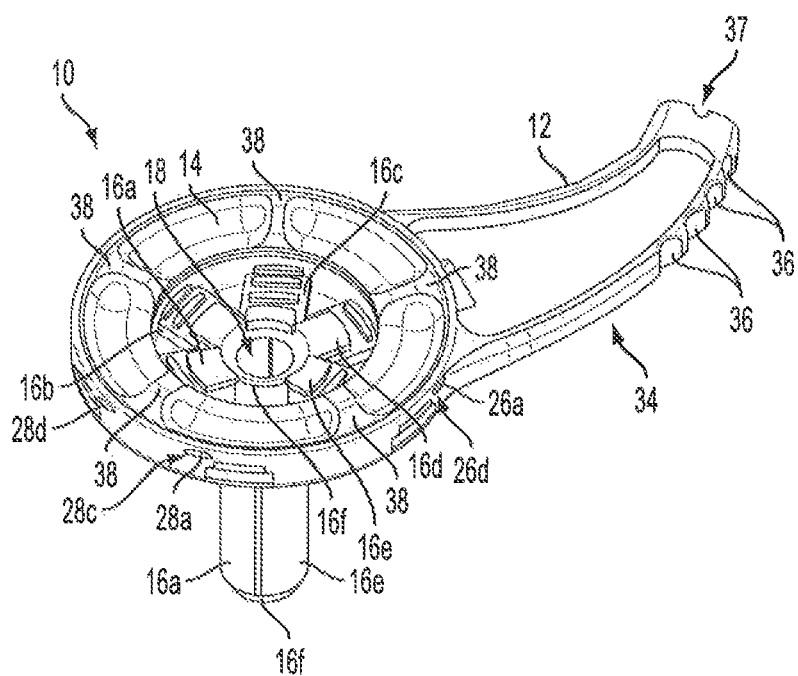
FIG. 3 is a perspective view of one embodiment of a retractor in a closed position.
Figure 4:
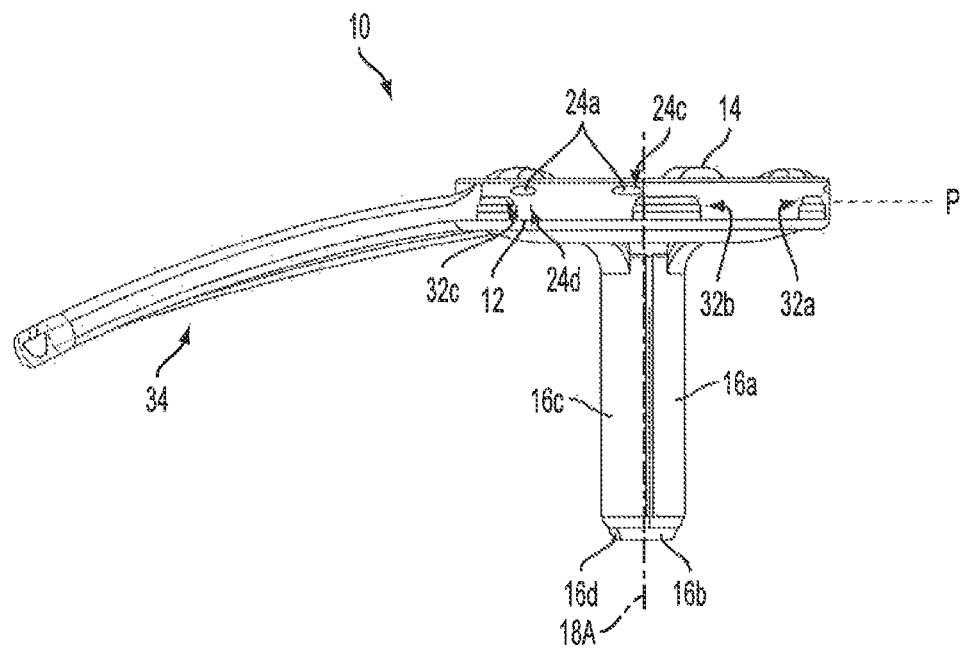
FIG. 4 is a side view of the retractor of FIG. 3.
Figure 5:
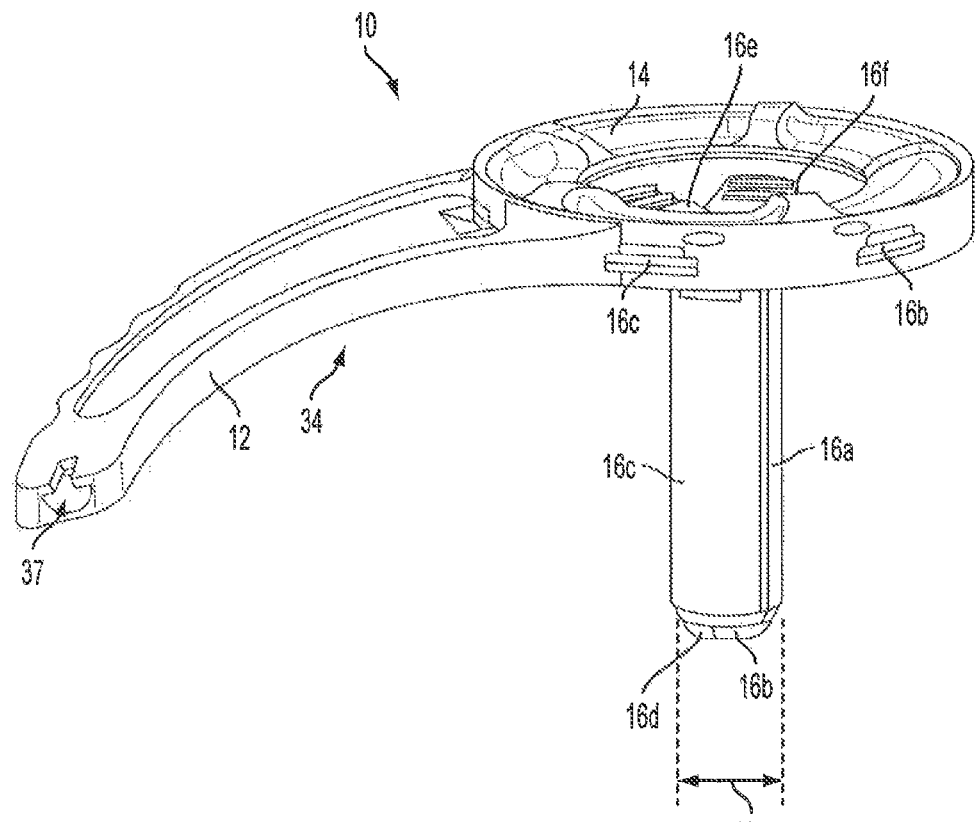
FIG. 5 is another perspective view of the retractor of FIG. 3.

A sidewall 22 of the base 12 can help define the track 20 along with a top or proximal-facing surface 12s of the base 12. As discussed further below, the proximal-facing surface 12s of the base 12 is hidden by the actuator 14 seated within the track 20. The sidewall 22 can include a rail configured to slidably engage a channel 30 formed in the actuator 14, thereby helping to securely retain the actuator 14 within the recessed track 20. The rail can thus be configured to facilitate smooth and stable movement of the actuator 14 relative to the base 12. The rail can have a variety of configurations and can be integrally formed with the base 12, or it can be one or more separate elements coupled thereto. In one embodiment, the sidewall 22 can have a continuous rail, e.g., a ring, extending radially inward from an interior surface of the sidewall 22. In another embodiment, the sidewall 22 can have a non-continuous rail, e.g., a series of aligned rails, extending radially inward from an interior surface of the sidewall 22. In the illustrated embodiment, as shown in FIGS. 3, 4, and 11, the sidewall 22 includes a rail in the form of a plurality of rail pins 24a, 26a, 28a mated to the sidewall 22 via a plurality of interior holes 24b formed in an interior surface of the sidewall 22 and a plurality of exterior holes 24c, 24d, 26c, 26d, 28c, 28d formed in an exterior surface of the sidewall 22. Only one interior hole 24b is visible in FIG. 11; the other two interior holes, corresponding respectively to the exterior holes 26c, 26d, 28c, 28d, are obscured in FIG. 11. The exterior holes 24c, 24d, 26c, 26d, 28c, 28d can each be configured to seat an end of one of the rail pins 24a, 26a, 28a, e.g., exterior holes 24c, 24d seating rail pin 24a, and the interior holes 24b, 26b, 28b can each be configured to seat a mid-portion of one of the rail pins 24a, 26a, 28a, e.g., interior hole 24b seating rail pin 24a. The rail pins 24a, 26a, 28a can be secured within the various holes in a variety of ways, such as by interference fit, snap fit, adhesive, etc. In the illustrated embodiment, the base 12 includes a rail and the actuator 14 includes a channel, but the base 12 can include a channel and the actuator can include a rail.

The base 12 can also be configured to seat each of the blades 16a, 16b, 16c, 16d, 16e, 16f, such as by including a plurality of recesses 30a, 30b, 30c, 30d, 30e, 30f each configured to seat one of the blades 16a, 16b, 16c, 16d, 16e, 16f. In the illustrated embodiment, the recesses 30a, 30b, 30c, 30d, 30e, 30f can be formed in the proximal-facing surface 12s of the base 12. In this way, as illustrated in FIGS. 6, 8, and 10, the blades 16a, 16b, 16c, 16d, 16e, 16f, e.g., proximal ends of the blades 16a, 16b, 16c, 16d, 16e, 16f, can each be seated in one of the recesses 30a, 30b, 30c, 30d, 30e, 30f and can be sandwiched between the actuator 14, e.g., a distal-facing surface 14s of the actuator 14, and the base 12, e.g., the proximal-facing surface 12s of the base 12.

The sidewall 22 that defines the perimeter of the base 12 can include a plurality of windows 32a, 32b, 32c, 32d, 32e, 32f formed therethrough, as shown in FIGS. 4 and 11. Each of the plurality of windows 32a, 32b, 32c, 32d, 32e, 32f can be configured to allow a different one of the blades 16a, 16b, 16c, 16d, 16e, 16f to advance therethrough when the actuator 14 is actuated to move the blades 16a, 16b, 16c, 16d, 16e, 16f relative to the base 12, as discussed further below. A number of the windows 32a, 32b, 32c, 32d, 32e, 32f, six in the illustrated embodiment, can therefore equal a number of the blades 16a, 16b, 16c, 16d, 16e, 16f. The windows 32a, 32b, 32c, 32d, 32e, 32f can each have a size and shape complementary to a cross-sectional shape of a portion of the blades 16a, 16b, 16c, 16d, 16e, 16f that can move therethrough, as discussed further below.

The base 12 can include a handle configured to be gripped by hand and/or be mounted to a stable object, e.g., a table, a wall, etc. The sidewall 22 or other base portion defining the track 20 can serve as a retractor handle, or, as in the illustrated embodiment, the retractor 10 can include a handle 34 extending radially outward from the sidewall 22. The handle 34 in the illustrated embodiment is in the form of an arcuate flange extending radially outward from the sidewall 22, but the handle can extend in any one or more directions, e.g., extend proximally, be L-shaped so as to extend radially and proximally, etc. The handle 34 can, as in the embodiment shown in FIG. 4, curve in a distal direction, which can help provide easier access to the proximally-accessible actuator 14. In another embodiment, the handle can be co-planar with the sidewall 22. The handle 34 can include one or more gripping features, e.g., a textured surface, one or more finger depressions 36, etc. configured to facilitate hand manipulation of the retractor 10. The handle 34 can include one or more mounting mechanisms configured to facilitate mounting of the retractor 10 to a stable object to allow hands-free use of the retractor 10 during a surgical procedure. In the illustrated embodiment, as shown in FIGS. 3-5 and 11, the handle 34 includes a notch 37 configured to be snap fit onto a complementary mounting mechanism (not shown), but the mounting mechanism can have a variety of other configurations, e.g., threads, clamp, etc.

Figure 12:
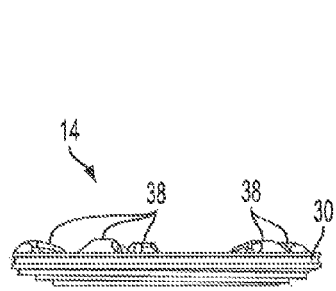
FIG. 12 is a side view of an actuator of the retractor of FIG. 3.
Figure 13:
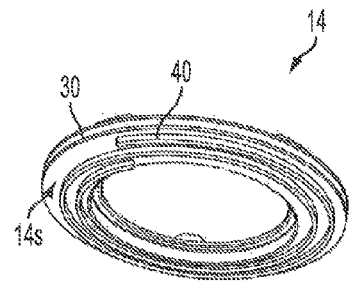
FIG. 13 is a perspective view of the actuator of FIG. 12.
Figure 14:
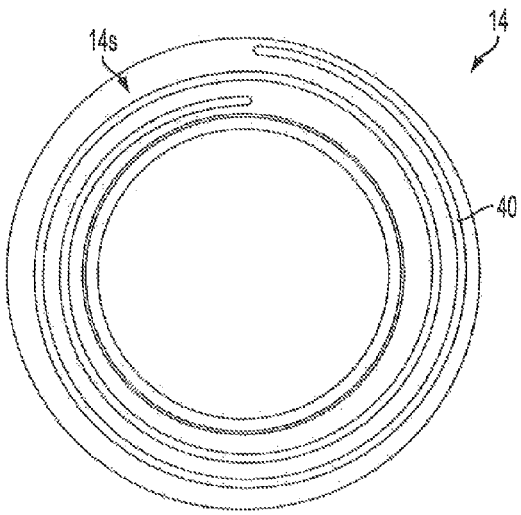
FIG. 14 is a bottom view of the actuator of FIG. 12.

The actuator 14, shown in FIGS. 3-10 and as a standalone element in FIGS. 12-14, can also have a variety of sizes, shapes, and configurations. The actuator 14 can be configured to be seated in the track 20 of the base 12 and to be operatively connected to the blades 16a, 16b, 16c, 16d, 16e, 16f to cause movement thereof relative to the base 12 when the actuator 14 is actuated, e.g., rotated within the track 20, relative to the base 12. The actuator 14 can have a size and shape complementary to the track 20 formed in the base 12 in which the actuator 14 can be seated. Thus, as in the illustrated embodiment, the actuator 14 can include a ring having a circular shape complementary to the circular track 20 and having a central void. In other embodiments, the actuator can be configured as a circular disc having a central perforation or central overlapping flaps aligned with the working channel 18 such that an instrument can be inserted through the perforation or flaps and then pass into the working channel 18.

As mentioned above, and as shown in FIGS. 12 and 13, the actuator 14 can include the channel 30 formed therein to engage the rail pins 24a, 26a, 28a seated in the base 12. The channel 30 can, as in the illustrated embodiment, extend around a full outer perimeter of the actuator 14 to allow rotation of the actuator 14.

As also mentioned above, the actuator 14 can be configured to be movable relative to the base 12 to cause the blades 16a, 16b, 16c, 16d, 16e, 16f to expand and collapse relative to the base 12 so as to increase and decrease the diameter 18D of the working channel 18. Generally, the actuator 14 can be actuated, e.g., rotated, to cause the actuator 14 to move, e.g., rotate, relative to the base 12 and thereby cause the blades 16a, 16b, 16c, 16d, 16e, 16f to move relative to the base 12. When the actuator 14 is rotated relative to the base 14, the rail pins 24a, 26a, 28a can slide within the channel 30.

Instead of the rail/channel system which facilitates rotation of the actuator 14 relative to the base 12 in the illustrated embodiment, a retractor can include a variety of other mechanisms configured to facilitate rotation of the actuator relative to the base. For non-limiting example, a retractor can include a ratchet/pawl system. The base can include a pawl, and the actuator can include a circular ratchet including a plurality of teeth configured to engage the pawl. When the actuator is rotated relative to the base, the pawl can disengage from one of the teeth and engage another one of the teeth when the actuator ceases rotating. The ratchet/pawl system can include a stop mechanism, e.g., a stop surface formed on the ratchet against which the pawl abuts, configured to stop rotation of the actuator beyond a certain point so as to prevent the actuator from rotating so far that one or more of the blades become disengaged from the base. The ratchet can include one or both of a stop mechanism to stop rotation in one direction, e.g., clockwise, and another stop mechanism to stop rotation in the other direction, e.g., counterclockwise. Alternatively, the actuator can include a pawl, and the base can include a ratchet.

The actuator 14 can include one or more gripping features configured to facilitate manual movement of the actuator 14. In the illustrated embodiment, the actuator 12 includes a plurality of finger grips 38, e.g., proximally raised protrusions contoured on opposed sides thereof to receive fingertips, to facilitate manual rotation of the actuator 14 relative to the base 12. Although the actuator 14 in the illustrated embodiment includes five finger grips 38, the actuator 38 can include any number of finger grips. Also, instead of or in addition to the finger grips 38, the actuator 14 can include other gripping features such as a textured surface, one or more finger loops, one or more finger depressions, a slide lever, a knob, etc.

As will be appreciated by a person skilled in the art, the actuator 14 can be manually actuated by hand and/or by using one or more tools. For non-limiting example, a tool can be pushed against one or more of the finger grips 38 to push the actuator 14 and cause rotation thereof. For another non-limiting example, the actuator can include one or more tool openings or loops configured to receive an end of a tool therein such that moving the tool can push the actuator 14 and cause rotation thereof.

As mentioned above, the actuator 14 can be operatively connected to the blades 16a, 16b, 16c, 16d, 16e, 16f to cause movement thereof when the actuator 14 is rotated relative to the base 12. The actuator 14 can be operatively connected to the blades 16a, 16b, 16c, 16d, 16e, 16f in a variety of ways. As in the illustrated embodiment, the actuator 14 can include a scroll gear or chuck, referred to herein as a "scroll gear," configured to operatively connect to the blades 16a, 16b, 16c, 16d, 16e, 16f via interlocking features formed on the actuator 14 and on the blades 16a, 16b, 16c, 16d, 16e, 16f. The scroll gear can have a variety of configurations and can be self-locking, as in the illustrated embodiment and as discussed further below. The distal-facing surface 14s of the actuator 14 can include a thread 40 formed thereon in the form of a continuous spiral thread, as shown in FIGS. 13 and 14, which can serve as the interlocking feature of the actuator 14 configured to engage the corresponding interlocking feature of the blades 16a, 16b, 16c, 16d, 16e, 16f. The distal-facing surface 14s of the actuator 14 can be inclined or curved distally inward, as shown in FIGS. 6, 8, 10, and 12, which can help the actuator 14 self-lock and help the actuator 14 maintain operative connection with the blades 16a, 16b, 16c, 16d, 16e, 16f, as discussed further below. In other words, the distal-facing surface 14s of the actuator 14 can be sloped in a proximal-to-distal direction from an outer-most region to an inner-most region of the actuator's central opening. Correspondingly, the proximal-facing surface 12s of the base 12s can be inclined or curved distally inward, e.g., be sloped in a proximal-to-distal direction from an outer-most region to an inner-most region of the base's central opening.

The blades 16a, 16b, 16c, 16d, 16e, 16f can also have a variety of sizes, shapes, and configurations. In an exemplary embodiment, each of the blades 16a, 16b, 16c, 16d, 16e, 16f can be substantially the same as one another, as in the illustrated embodiment. A person skilled in the art will appreciate that the blades 16a, 16b, 16c, 16d, 16e, 16f may be substantially identical but not be precisely identical to one another due to one or more factors such as manufacturing tolerances, color coding and/or other coding such as printed numerical coding for ease of identification, etc. For ease of illustration and discussion, a first one of the blades 16a, illustrated in FIGS. 6, 8, 10, 15A, and 15B, is discussed as a representative one of the blades 16a, 16b, 16c, 16d, 16e, 16f. Although the retractor 10 in this illustrated embodiment includes six blades 16a, 16b, 16c, 16d, 16e, 16f, a retractor can have any number of blades.

Figure 15A:
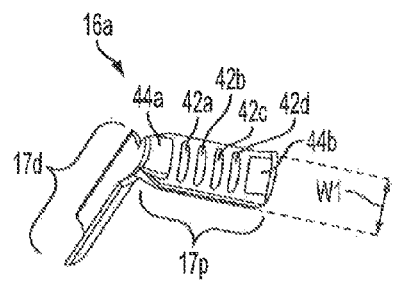
FIG. 15A is a perspective view of a blade of the retractor of FIG. 3.
Figure 15B:
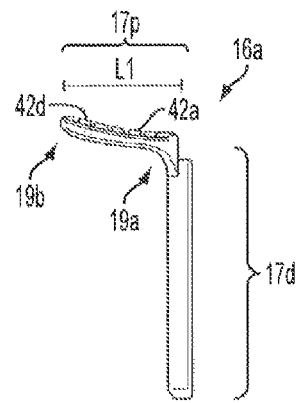
FIG. 15B is a side view of the blade of FIG. 15A.

As best shown in FIGS. 15A and 15B, the first blade 16a can include a proximal portion 17p configured to engage the actuator 14 and the base 12 and a distal portion 17d configured to extend from the base 12 and to contact and retract tissue. The distal portion 17d can extend at a non-zero angle α, e.g., greater than 0 degrees and less than 180 degrees, relative to the proximal portion 17p. The angle α can vary, but in an exemplary embodiment, the angle α can be about 90 degrees, as in the illustrated embodiment, such that the distal portion 17d of the blade 16a extends substantially perpendicular to a plane P, shown in FIG. 4, in which the actuator 14 rotates. In this way, the working channel 18 defined by the distal portions of the blades 16a, 16b, 16c, 16d, 16e, 16f, e.g., a longitudinal axis 18A of the working channel 18, shown in FIG. 4, can extend substantially perpendicular to the plane P in which the actuator 14 rotates, which can help facilitate access to and simultaneous handling of the actuator 14 and an instrument inserted through the working channel 18. A person skilled in the art will appreciate that the angle α of the distal portion 17d of the blades 16a, 16b, 16c, 16d, 16e, 16f relative to the longitudinal axis 18A of the working channel 18 can vary as the blades 16a, 16b, 16c, 16d, 16e, 16f move between the collapsed and expanded positions.

The distal portion 17d of the first blade 16a can have a variety of sizes, shapes, and configurations. In this illustrated embodiment, the distal portion 17d has a fixed longitudinal length, but as will be appreciated by a person skilled in the art, the distal portion 17d can have a variable longitudinal length, such as by being configured as a telescoping blade. Additionally, a retractor can include blades that are all telescoping, or a retractor can include some telescoping blades and some non-telescoping blades. In some embodiments, a retractor can be configured to have one or more removable blade extenders mates to one or more blades of the retractor so as to extend the longitudinal lengths of the one or more blades.

The distal portion 17d can have a curved profile such that the blade 16a is curved about a longitudinal axis of the distal portion 17d of the blade 16a, as in this illustrated embodiment in which the distal portion 17d has an arcuate cross-sectional shape. Collectively, the curved profiles of the distal portions of the blades 16a, 16b, 16c, 16d, 16e, 16f can define the working channel 18, which in this embodiment has a closed cylindrical shape, e.g., a circular cross-sectional shape, when the retractor 10 is in the closed position. In other embodiments, the distal portions of the blades 16a, 16b, 16c, 16d, 16e, 16f can have profiles defining a non-cylindrical working channel when the retractor is in a closed position, such as a working channel having an elliptical cross-sectional shape, a square or rectangular cross-sectional shape, an irregular cross-sectional shape, a triangular cross-sectional shape, etc.

Figure 16:
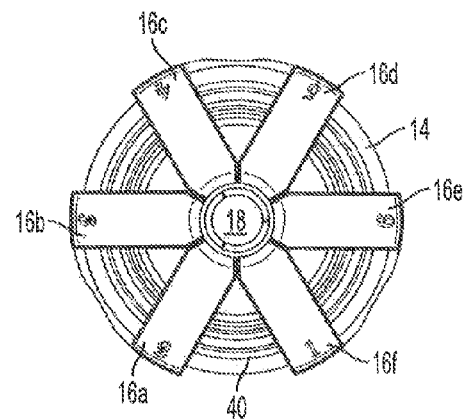
FIG. 16 is a bottom view of the retractor of FIG. 3 without the base of the retractor.
Figure 17:
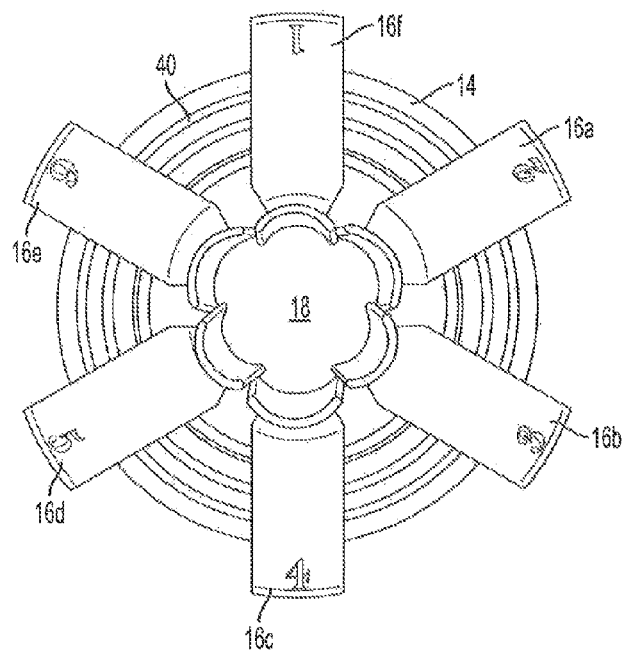
FIG. 17 is a bottom view of the retractor of FIG. 7 without the base of the retractor.

The distal portions of the blades 16a, 16b, 16c, 16d, 16e, 16f can be configured to nest or overlap with one another, at least when the retractor 10 is closed and the blades 16a, 16b, 16c, 16d, 16e, 16f are in the collapsed position. By being nested or overlapped, the blades 16a, 16b, 16c, 16d, 16e, 16f can have a smaller diameter than non-nested or non-overlapped blades. In other words, the blades 16a, 16b, 16c, 16d, 16e, 16f defining a relatively small working channel diameter 18D can be inserted into a patient's body through a relatively small opening and can be configured to radially expand to achieve a much larger working channel diameter 18D. As shown in the illustrated embodiment in FIGS. 3-6 and 16, when the retractor 10 is in the closed position, the blades 16a, 16b, 16c, 16d, 16e, 16f can be nested or overlapped with a first number of the blades 16a, 16c, 16e defining an outer surface of the working channel 18, e.g., defining an exterior of the working channel's shape, and a remaining number of the blades 16b, 16d, 16f defining an inner surface of the working channel 18, e.g., defining an interior of the working channel's shape. The blades 16a, 16b, 16c, 16d, 16e, 16f can therefore nest or overlap such that the first number of blades 16a, 16c, 16e can be completely obscured from the interior of the working channel's shape, and the remaining number of the blades 16b, 16d, 16f can be completely obscured from the exterior of the working channel's shape. Each of the first number of blades 16a, 16c, 16e, e.g., outer blades, can have their longitudinal edges abut one another so as to define a first closed cylindrical shape, as shown in FIG. 16. Similarly, each of the remaining number of blades 16b, 16d, 16f, e.g., inner blades, can have their longitudinal edges abut one another so as to define a second closed cylindrical shape. Having obscured blades can help the retractor 10 be smoothly inserted into a patient and can help prevent any instruments inserted through the working channel 18 when the retractor 10 is closed from passing outside the working channel 18 before exiting through an open distal end thereof, thereby helping to prevent accidental tissue damage. Such obscuring can also facilitate effective tissue retraction because when the retractor 10 is moved from the closed position to the open position, e.g., moved from the position shown in FIG. 16 to the position shown in FIG. 17, the first number of the blades 16a, 16c, 16e can contact and retract tissue before the remaining number of blades 16b, 16d, 16f contact and retract the tissue. The remaining number of blades 16b, 16d, 16f can therefore be configured to "catch" and retract tissue that slips between the first number of blades 16a, 16c, 16e as the first number of the blades 16a, 16c, 16e retract the tissue.

When the retractor 10 includes an even number of blades 16a, 16b, 16c, 16d, 16e, 16f, as in the illustrated embodiment, the first number of blades can equal the remaining number of blades such that half the blades define an exterior shape of the working channel and half the blades define an interior shape of the working channel. Thus, when the blades are in the collapsed position, half a number, e.g., three, of the blades can define the size of the working channel rather than all, e.g., six, of the blades defining the working channel's size. When a retractor has an odd number of blades, the first number of blades or the remaining number of blades may be larger than the other, e.g., two exterior blades three interior blades, three exterior blades and four interior blades, etc.

The proximal portion 17p of the first blade 16a can also have a variety of sizes, shapes, and configurations. The proximal portion 17p of the first blade 16a can be configured to be non-removable from the base 12, as in the illustrated embodiment in which all of the blades 16a, 16b, 16c, 16d, 16e, 16f are non-removably coupled to the base 12. Alternatively, any one of more of the blades can be configured to removably and replaceably couple to the base in any of a variety of ways, as will be appreciated by a person skilled in the art. For non-limiting example, an end portion of a blade can be configured as a depressible button such that pressing the button down can allow the blade to slide out of or into the blade's associated window formed in the base of the retractor. For another non-limiting example, a proximal portion of a blade can be configured to be non-removable from a base, similar to the proximal portion 17p in the illustrated embodiment, and can be configured to have a distal portion of the blade removably and replaceably coupled thereto, e.g., by snap fit. By including one or more blades with removable and replaceable distal portions, optimal blade sizes can be selected for use in accordance with a particular procedure performed on a particular patient.

The proximal portion 17p of the first blade 16a can curve or bend slightly upward, as shown in FIG. 15B, along a longitudinal length L1 thereof. As shown, a first end 19a of the proximal portion 17p can be attached to the distal portion 17d, and the proximal portion 17p can curve or bend upwards toward a second, opposite end 19b of the proximal portion 17p, e.g., be sloped in a radially outward direction from the first end 19a to the second end 19b. This curve or bend can facilitate movement of the blade 16a relative to the base 12, as discussed further below. The proximal portion 17p can have a linear or non-arcuate cross-sectional shape. In other words, a width W1 of the proximal portion, shown in FIG. 15A, can have a substantially flat profile, as opposed to the curved profile of the distal portion 17d discussed above.

The proximal portion 17p of the first blade 16a can include a plurality of ridges or teeth 42a, 42b, 42c, 42d, referred to herein as "teeth," formed thereon. The teeth 42a, 42b, 42c, 42d can extend across the width W1 of the proximal portion 17p on a proximal surface of the proximal portion 17p. The teeth 42a, 42b, 42c, 42d can be aligned linearly and radially such that a first one of the teeth 42a is an innermost one of the teeth 42a, e.g., closest to the first end 19a of the proximal portion 17p attached to the distal portion 17d, with a remainder of the teeth 42b, 42c, 42d being spaced radially outward toward the second end 19b of the proximal portion 17p. Although the first blade 16a includes four teeth, the retractor blades can each include any number of teeth. The first blade 16a can also include first and second end stops 44a, 44b. The first and second end stops 44a, 44b can be configured similar to the teeth 42a, 42b, 42c, 42d and can be positioned on either radial end of the teeth 42a, 42b, 42c, 42d, as shown in FIG. 15A, such that the first end stop 44a can be positioned radially inward of the first tooth 42a, and the second end stop 44b can be positioned radially outward of a last one 44d of the teeth. In some embodiments, the second end stop 44b can be configured as a depressible button such that, as discussed above, the depressible button can be depressed to selectively allow removal of the blade from and attachment of the blade to the base 12. The other blades 16b, 16c, 16d, 16e, 16f can be identical to the first blade 16a, as mentioned above, and thus can each also include teeth and end stops similar to the first blade 16a.

The teeth 42a, 42b, 42c, 42d and the end stops 44a, 44b can protrude proximally from a surface of the first blade 16a so as to be configured to engage the thread 40 of the actuator 14, which can be positioned proximal to the blade 16a, as shown in FIGS. 6, 8, 10, 16, and 17. The thread 40 of the actuator 14 can therefore be configured to engage the plurality of teeth and the plurality of end stops formed on each of the blades 16a, 16b, 16c, 16d, 16e, 16f. Similarly, the plurality of teeth and the plurality of end stops formed on each of the blades 16a, 16b, 16c, 16d, 16e, 16f can define a channel or groove for the thread 40 to slidably move within when the actuator 14 rotates relative to the base 12. For ease of illustration and discussion, the first blade 16a having the plurality of teeth 42a, 42b, 42c, 42d formed thereon, as shown in FIGS. 6, 8, 10, 15A, and 15B, is discussed with reference to the thread 40 and movement of the actuator 14 relative to the base 12.

The thread 40 of the actuator 14 can be configured to be slidable between the teeth 42a, 42b, 42c, 42d, e.g., to thread between the teeth 42, as the actuator 14 is rotated relative to the base 12. In this way, the thread 40 can cause the blades 16a, 16b, 16c, 16d, 16e, 16f to move radially inward or radially outward relative to the base 12, e.g., laterally relative to the base 12 and transverse to the longitudinal axis 18A of the working channel 18, depending on a direction of the actuator's rotation.

In another embodiment, a retractor can be configured to be positioned in a stable configuration which can be used during radially outward and radially inward motion of the retractor's blades relative to the retractor's base. Such a retractor and its various elements, e.g., blades, base, etc., can be generally configured and used similar to other like-named elements discussed herein. The retractor can include a stable blade, e.g., one of the blades removably and replaceably mated to the base, configured to be mounted to a stable object, e.g., a table, one or more a rigid arms, a wall, etc., without the base or any of the other blades being mounted to the stable object. In the stable configuration, the stable blade can be so mounted so as to allow movement of the blades with the stable blade as a stationary reference. The stable blade can include a mounting mechanism in a proximal portion thereof, e.g., in a portion of the blade configured to mate to the base. The mounting mechanism can have a variety of configurations, e.g., a notch configured to be snap fit to a complementary mounting mechanism, threads, clamp, etc. In this way, in use, the stable blade can be the only element of retractor that is stabilized to the patient. During rotation of the retractor's actuator, the blades can move relative to each other, however the base and consequently the working channel, e.g., a longitudinal axis of the working channel, can migrate away from or towards the stable blade. In other words, the stable blade can be configured to remain stationary relative to the patient and to the stable object to which the stable blade is mounted.

Rotating the actuator 14 in a first direction, e.g., clockwise, relative to the base 12 can cause the blades 16a, 16b, 16c, 16d, 16e, 16f to move radially outward relative to the base 12 as the thread 40 slides between different ones of the teeth 42a, 42b, 42c, 42d. Because the actuator 14 is held in place within the track 20 as the actuator 14 rotates, e.g., the actuator 14 does not move radially relative to the base 12, the blades 16a, 16b, 16c, 16d, 16e, 16f can move through the thread 40. The inclined or curved bottom profile of the actuator 14 can help maintain contact between the thread 40 and the blades 16a, 16b, 16c, 16d, 16e, 16f as the actuator 14 rotates relative to the base 12 and the blades 16a, 16b, 16c, 16d, 16e, 16f move relative to the base 12. This contact can help slide the blades 16a, 16b, 16c, 16d, 16e, 16f radially outward along the inclined or curved proximal-facing surface 12s of the base 12s and through their respective 32a, 32b, 32c, 32d, 32e, 32f formed in the base's sidewall 22. In other words, rotating the actuator 14 can cause the blades 16a, 16b, 16c, 16d, 16e, 16f to pivot radially outward. Correspondingly, rotating the actuator 14 in a second, opposite direction, e.g., counterclockwise, relative to the base 12 can cause the blades 16a, 16b, 16c, 16d, 16e, 16f to move radially inward relative to the base 12, e.g., pivot radially inward.

The pivoting of the blades 16a, 16b, 16c, 16d, 16e, 16f radially outward can cause the diameter 18D of the working channel 18 to differ between a proximal end 18p and a distal end 18i thereof, as shown in FIGS. 8 and 10, when the retractor 10 is in the open position, e.g., when the blades 16a, 16b, 16c, 16d, 16e, 16f are in the expanded position. In particular, a diameter 18D1 of the working channel 18 at the proximal end 18p thereof can be less than a diameter 18D2 of the working channel 18 at the distal end 18i thereof. The working channel 18 can thereof have a distally-tapering cone or pyramid shape when the retractor 10 is in the open position. In contrast, when the retractor 10 is in the closed position, e.g., when the blades 16a, 16b, 16c, 16d, 16e, 16f are in the collapsed position, as shown in FIG. 6, the diameters 18D1, 18D2 of the working channel 18 at the proximal and distal ends 18p,18i and can be the same and can be constant along a longitudinal length thereof so as to define a cylindrically shaped working channel.

As shown in FIGS. 6, 8, and 10 of the illustrated embodiment, when the retractor 10 is the closed position with the blades 16a, 16b, 16c, 16d, 16e, 16f in the collapsed position, rotating the actuator 14 in the first direction can cause the teeth of the blades 16a, 16b, 16c, 16d, 16e, 16f to move through the thread 40 of the actuator 14, thereby advancing each of the blades 16a, 16b, 16c, 16d, 16e, 16f radially outward through their respective windows 32a, 32b, 32c, 32d, 32e, 32f formed in the base's sidewall 22, and moving the retractor 10 to the open position with the blades 16a, 16b, 16c, 16d, 16e, 16f in the expanded position. In other words, when the retractor 10 is in the closed position, as shown in FIGS. 3-6, the thread 40 can be positioned in spaces defined by outermost ones of the teeth 42c, 42d and the second end stop 44b, e.g., positioned in two spaces, and the blades 16a, 16b, 16c, 16d, 16e, 16f can be substantially contained within a perimeter or circumference of the base 12 as defined by the base's sidewall 22, e.g., the blades 16a, 16b, 16c, 16d, 16e, 16f not being positioned radially outward of the windows 32a, 32b, 32c, 32d, 32e, 32f. From when the retractor 10 is in the closed position, the actuator 14 can be rotated to move the blades 16a, 16b, 16c, 16d, 16e, 16f radially outward through the windows 32a, 32b, 32c, 32d, 32e, 32f such that the thread 40 can eventually be positioned between spaces defined by innermost ones of the teeth 42a, 42b and the first end stop 44a, e.g., positioned in two spaces different from when the retractor 10 is in the closed position, when the retractor 10 is fully open, as shown in FIG. 10. Although, as well be appreciated by a person skilled in the art, the actuator 14 need not be rotated to fully open the retractor 10 but instead be rotated to move the retractor 10 to a partially open position, such as the partially open positioned illustrated in FIGS. 7 and 8. Similarly, rotating the actuator 14 in the second direction can cause the reverse to occur, thereby advancing each of the blades 16a, 16b, 16c, 16d, 16e, 16f radially inward through their respective openings 32a, 32b, 32c, 32d, 32e, 32f formed in the base sidewall 22, and moving the retractor 10 toward the closed position.

The blades 16a, 16b, 16c, 16d, 16e, 16f can be prevented from moving beyond a certain expanded or collapsed point by the thread 40 running out of space to move along the proximal portions of the blades 16a, 16b, 16c, 16d, 16e, 16f on either end of the actuator's clockwise or counterclockwise rotation. In other words, the end stops of the blades 16a, 16b, 16c, 16d, 16e, 16f, e.g., the end stops 44a, 44b of the first blade 16a, can be configured to define threshold positions of the actuator 14 relative to the base 12 to prevent further rotation of the actuator 14 relative to the base 12 when the thread 40 abuts either of the end stops 44a, 44b, e.g., when the retractor 10 is fully open as shown in FIG. 10 or closed as shown in FIG. 6. The teeth and end stops of the blades 16a, 16b, 16c, 16d, 16e, 16f can therefore define the blades' range of movement.

The actuator 14 can be configured to be self-locking, as mentioned above. In this way, the actuator 14 can be controllably rotated to any selected position relative to the base 12 to freely move the blades 16a, 16b, 16c, 16d, 16e, 16f relative to the base 12 and hold the blades 16a, 16b, 16c, 16d, 16e, 16f in any selected position relative to the base 12. When the actuator 14 is not rotating, the actuator 14, e.g., a curvature of the distal-facing surface 14 and a pitch of the thread 40 which can approximate the curvature, can be configured to help hold the blades 16a, 16b, 16c, 16d, 16e, 16f in position relative to the base 12, thereby preventing the blades 16a, 16b, 16c, 16d, 16e, 16f from slipping relative to any tissue they are retracting and/or to any instrument inserted through the working channel 18. The actuator 14 can therefore be configured to counteract radially outward forces applied by the blades 16a, 16b, 16c, 16d, 16e, 16f and thereby prevent the teeth of the blades 16a, 16b, 16c, 16d, 16e, 16f from sliding relative to the thread 40 when the actuator 14 is not being manually rotated. As mentioned above, the curved profile of the distal-facing surface 14s of the actuator 14 and the curved profile of the proximal-facing surface 12s of the base 12 in cooperation with the engagement between the thread 40 of the actuator 14 and the teeth of the blades 16a, 16b, 16c, 16d, 16e, 16f can help hold the blades 16a, 16b, 16c, 16d, 16e, 16f in position relative to the base 12. A ratio of an average diameter of the thread 40 to the pitch of the thread 40, e.g., a distance between innermost teeth 42a, 42b, can allow the self-locking of the actuator 14. In an exemplary embodiment, the ratio can be in a range of about 0.03 to 0.2, e.g., about 0.08 (e.g., a pitch of about 8 mm and an average thread diameter of about 100 mm). The smaller the ratio, the more effectively the actuator 14 can self-lock. A co-efficient of friction between the blades 16a, 16b, 16c, 16d, 16e, 16f and the actuator 14 can also help hold the blades 16a, 16b, 16c, 16d, 16e, 16f in position relative to the base 12.

Figure 18:
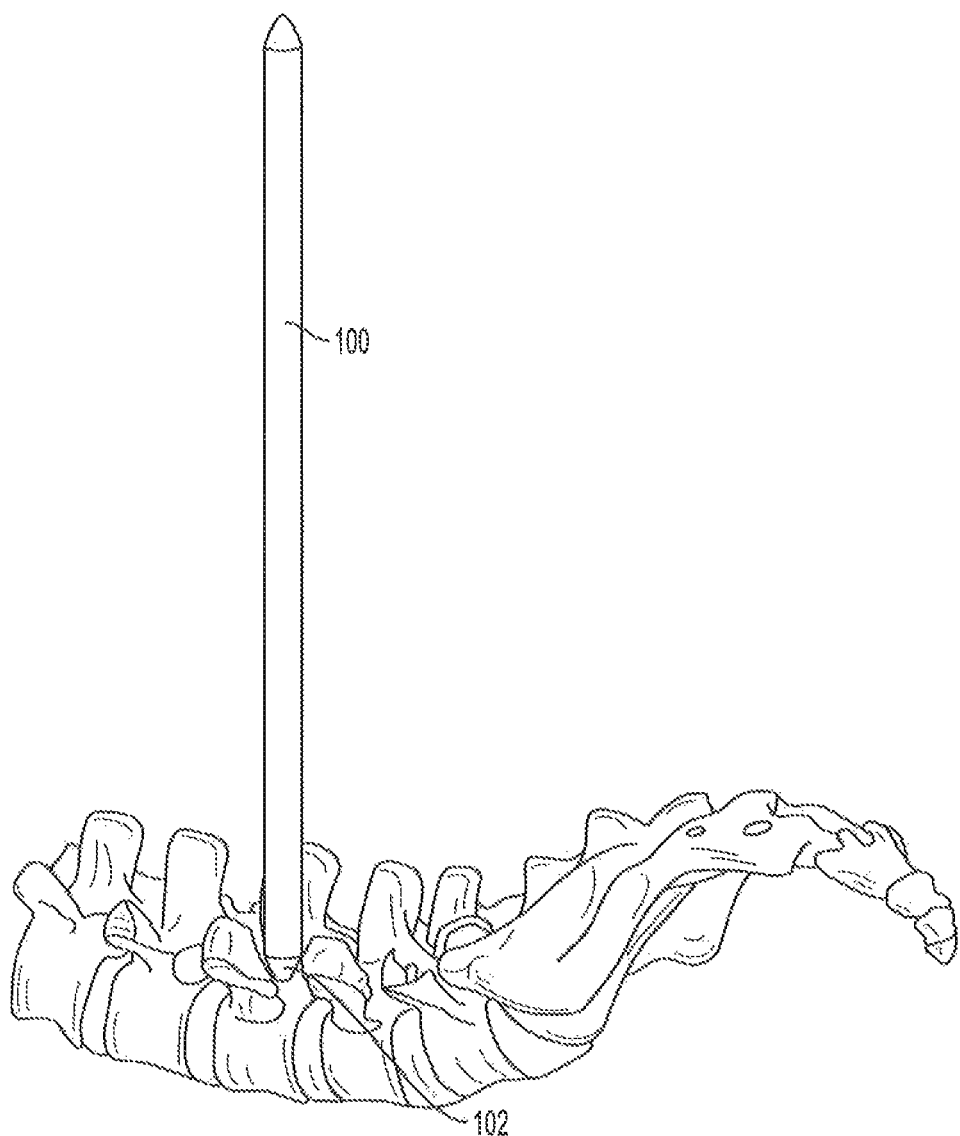
FIG. 18 is a perspective view of an obturator advanced to a spine.
Figure 19:
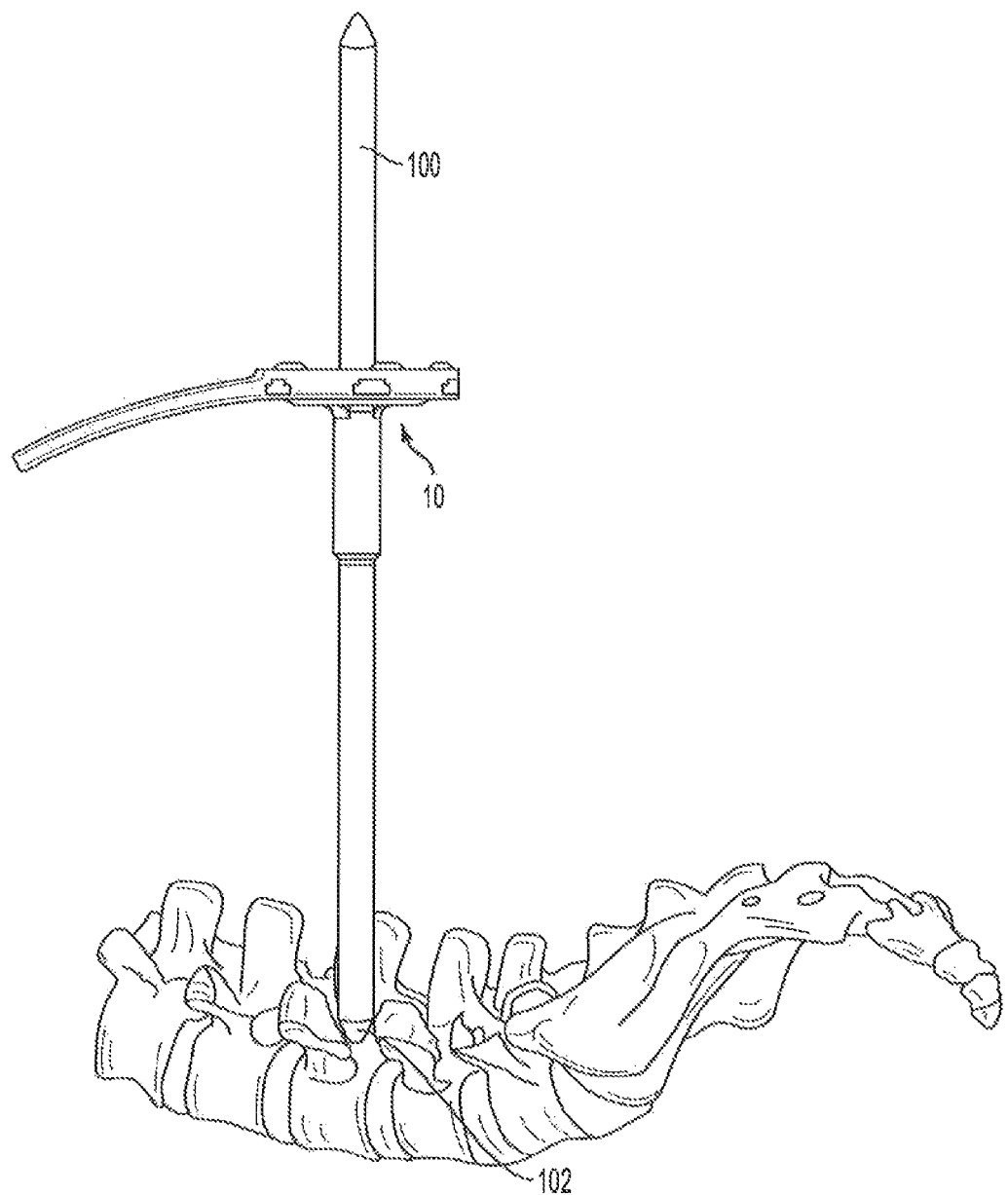
FIG. 19 is a perspective view of the retractor of FIG. 3 being advanced over the obturator of FIG. 18.
Figure 20:
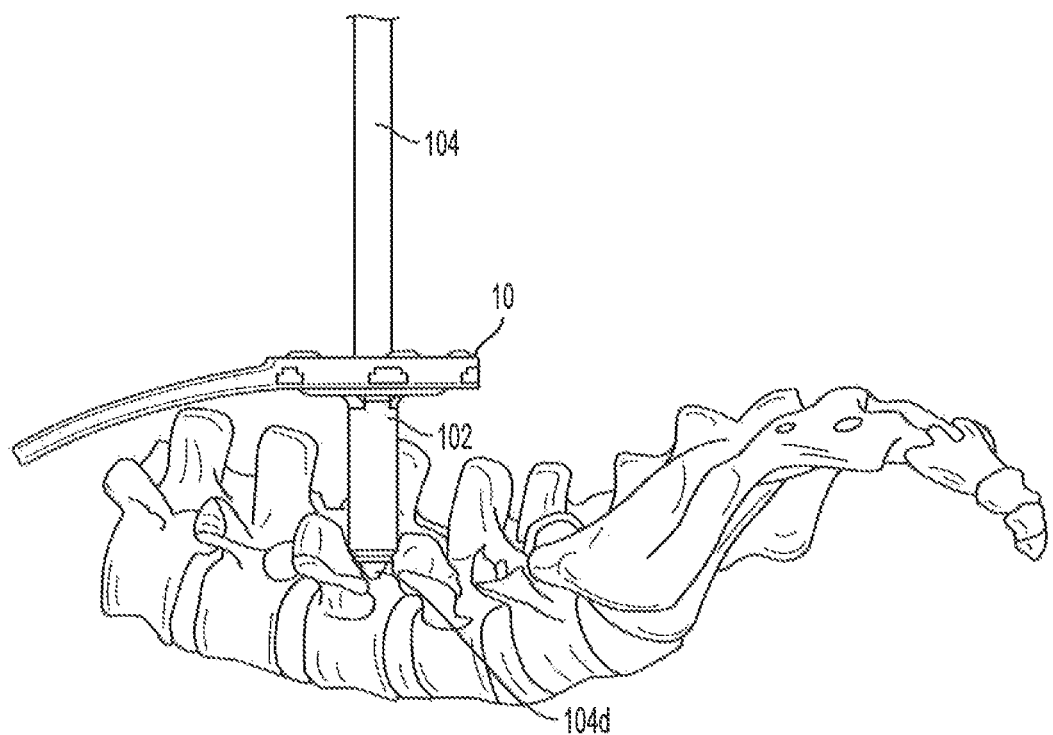
FIG. 20 is a perspective view of the retractor of FIG. 19 advanced to the spine and having a surgical instrument inserted therethrough.

In some embodiments, the retractor 10 can be inserted over an obturator during insertion of the retractor to the depth of the surgical site or near the depth of the surgical site to be formed. FIGS. 18-20 illustrate one embodiment of such a method used to retract tissue near the spine of a human. Soft tissue and some bone mass has been omitted from the figures for clarity. A person skilled in the art will appreciate that while use of the retractor 10 is shown and described with reference to FIGS. 18-20 as retracting tissue adjacent a spine, any retractor disclosed herein can be used similarly, and the methods and devices disclosed herein can be used to retract tissue in a variety of medical procedures at various places around a patient's body.

FIG. 18 illustrates an obturator 100 after it has been inserted into an incision and directed to a surgical site 102, e.g., next to a spinal column. Optionally, the obturator 100 can be directed along a guide wire (not shown) which has previously been tethered to the surgical site 102. Once the obturator 100 is in position at the surgical site 102, the retractor 10 can be advanced over the obturator 100, e.g., with the obturator passing through the working channel 18, to the surgical site 102. The retractor 10 in the closed position can be advanced alone over the obturator 100, as shown in FIG. 19. Alternatively, as will be appreciated by a person skilled in the art, the retractor 10 can be coupled to an introducer device (not shown) configured to advance the retractor 10 along the obturator 100. Whether advanced using an introducer device or not, the retractor 10 can be advanced distally to the surgical site 102 by pushing the retractor 10 down the length of obturator 100 to the surgical site 102, as shown in FIG. 19. Once the retractor 10 is at the surgical site 102, the obturator 100 can be removed from the incision, leaving the retractor 10 at the surgical site 102. Instead of using the obturator 100 to guide the retractor 10 to the surgical site 102, as will be appreciated by a person skilled in the art the retractor 10 can be advanced to the surgical site 102 in a number of other ways, e.g., using a guide wire, using an introducer device, hand insertion, etc. Optionally, at any point during the procedure, the retractor 10 can be attached to a surgical retractor positioning mechanism, e.g. a table, one or more a rigid arms, a wall, etc., to rigidly secure the retractor 10 at a fixed location relative to the surgical site 102.

Once positioned at the surgical site 102, the retractor 10 can be actuated as discussed above to retract tissue at the surgical site 102. With the retractor 10 in the closed position or in the open position, one or more surgical instruments 104 can be inserted through the working channel 18 of the retractor 10, as shown in FIG. 20 with the retractor 10 in the closed position, such that a distal end 104d of the instrument 104 extends through the working channel 18 to access bone, tissue, and/or other matter at the surgical site 102. Although a grasper with jaws is illustrated as the instrument 104 in FIG. 20, a person skilled in the art will appreciate that any instrument can be inserted through the working channel 18.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device, e.g., the blades, can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A retractor, comprising:
a base having a track formed therein and a proximal-facing surface in which a plurality of recesses are formed;
an actuator seated in the track such that the actuator is rotatable within the track relative to the base, the actuator including a thread formed on a distal-facing surface thereof; and
a plurality of retractor blades, each of the retractor blades having a distal portion that extends from the base and is configured to contact and retract tissue and a proximal portion seated in one of the recesses of the base such that the proximal portion is sandwiched between the distal-facing surface of the actuator and the proximal-facing surface of the base, the proximal portion including a plurality of teeth configured to engage the thread of the actuator;
wherein rotation of the actuator in a first direction relative to the base causes the thread of the actuator to engage the teeth of the retractor blades to push the retractor blades radially-outward, and wherein rotation of the actuator in a second, opposite direction relative to the base causes the thread of the actuator to engage the teeth of the retractor blades to pull the retractor blades radially-inward.

2. The retractor of claim 1, wherein the thread of the actuator is a continuous spiral thread.

3. The retractor of claim 1, wherein the distal-facing surface of the actuator is sloped in a proximal-to-distal direction from an outer-most region of the actuator to a central opening of the actuator and wherein the proximal-facing surface of the base is sloped in a proximal-to-distal direction from an outer-most region of the base to a central opening of the base.

4. The retractor of claim 1, wherein the distal portion of each retractor blade extends at a non-zero angle relative to the proximal portion of said retractor blade.

5. The retractor of claim 1, wherein the plurality of retractor blades define a working channel through the retractor having a longitudinal axis that extends perpendicular to a plane in which the actuator rotates.

6. The retractor of claim 1, wherein the teeth of each retractor blade extend across a width of said retractor blade.

7. The retractor of claim 1, wherein the teeth of each retractor blade are spaced apart from one another along a length of said retractor blade.

8. The retractor of claim 1, wherein the proximal portion of each retractor blade includes first and second end stops.

9. The retractor of claim 8, wherein the second end stop comprises a depressible button configured to selectively allow removal of the retractor blade from the base.

10. The retractor of claim 1, wherein the track is circular and the actuator is ring-shaped.

11. The retractor of claim 1, further comprising a handle extending radially-outward from the base.

12. The retractor of claim 1, wherein the actuator is rotatably-coupled to the base by a ratchet and pawl system.

13. A surgical retractor, comprising:
a base that defines a circular track;
a ring-shaped actuator rotatably received within the circular track of the base, the actuator including a thread formed on a distal-facing surface thereof;
a plurality of retractor blades slidably-coupled to the base, each retractor blade including teeth formed on a proximal-facing surface thereof configured to be engaged by the thread of the actuator such that rotation of the actuator relative to the base is effective to move the retractor blades radially-inward or radially-outward relative to the base, depending on the direction of rotation.

14. The retractor of claim 13, wherein the base includes a sidewall that defines a portion of the track.

15. The retractor of claim 14, wherein the sidewall includes a plurality of windows through which the plurality of retractor blades extend.

16. The retractor of claim 14, wherein one of the sidewall and the actuator includes a rail configured to slidably engage a channel formed in the other of the sidewall and the actuator.

17. The retractor of claim 16, wherein the rail extends radially-inward from an interior surface of the sidewall.

18. The retractor of claim 16, wherein the rail comprises one of a continuous ring, a series of aligned rails, and a plurality of rail pins.

19. The retractor of claim 13, wherein the distal-facing surface of the actuator is sloped in a proximal-to-distal direction from an outer-most region of the actuator to a central opening of the actuator and wherein a proximal-facing surface of the base is sloped in a proximal-to-distal direction from an outer-most region of the base to a central opening of the base.

20. A surgical device, comprising:
a base having a rotatable actuator seated therein;
a plurality of retractor blades extending distally from the base, the plurality of retractor blades defining a working channel having a longitudinal axis that is perpendicular to a plane in which the actuator rotates;
wherein a distal-facing surface of the actuator threadably engages proximal-facing surfaces of each of the retractor blades to move the retractor blades radially-inward or radially-outward as the actuator is rotated relative to the base.

* * * * *